(12) United States Patent
Kaji

(10) Patent No.: US 6,947,358 B2
(45) Date of Patent: Sep. 20, 2005

(54) PICKUP DRIVE CONTROLLER FOR OPTICAL DISC DRIVE

(75) Inventor: Toshihiko Kaji, Ehime (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 606 days.

(21) Appl. No.: 09/937,859

(22) PCT Filed: Feb. 9, 2001

(86) PCT No.: PCT/JP01/00919

§ 371 (c)(1),
(2), (4) Date: Nov. 30, 2001

(87) PCT Pub. No.: WO01/59775

PCT Pub. Date: Aug. 16, 2001

(65) Prior Publication Data

US 2002/0167873 A1 Nov. 14, 2002

(30) Foreign Application Priority Data

Feb. 9, 2000 (JP) ........................................ 2000-032207

(51) Int. Cl.⁷ ................................................. G11B 7/00
(52) U.S. Cl. ................................ 369/44.28; 369/44.32; 369/53.12; 369/53.29
(58) Field of Search ............................ 369/30.1, 44.27, 369/44.28, 44.29, 44.32, 47.38, 47.39, 47.44, 47.45, 53.12, 53.18, 53.28, 53.29

(56) References Cited

U.S. PATENT DOCUMENTS

| | | | | |
|---|---|---|---|---|
| 4,744,069 A | * | 5/1988 | Sugiyama et al. | 369/44.29 |
| 5,442,613 A | * | 8/1995 | Horiguchi | 369/53.16 |
| 5,689,482 A | | 11/1997 | Iida | 369/30.1 |
| 5,870,356 A | * | 2/1999 | Ikeda | 369/30.15 |

FOREIGN PATENT DOCUMENTS

| | | |
|---|---|---|
| JP | 02-149930 | 6/1990 |
| JP | 03-152727 | 6/1991 |
| JP | 5-250686 | 9/1993 |
| JP | 8-96534 | 4/1996 |
| JP | 10-275343 | 10/1998 |

* cited by examiner

Primary Examiner—Paul W. Huber
(74) Attorney, Agent, or Firm—Wenderoth, Lind & Ponack, L.L.P.

(57) ABSTRACT

In an optical disk drive, in order to cancel a lens offset which may occur when performing a seek followed by a read, a seek position must be set several sectors before a target position for the read, resulting in a delay in access time. A lens offset amount is measured when a seek followed by read is started, and how many sectors before a read target position a seek position must be set is determined on the basis of two parameters, namely, the lens offset amount and a number of seek tracks. Thereby, an optimum seek position at which the lens offset is canceled can be set with no waste, resulting in an improvement in access time.

10 Claims, 7 Drawing Sheets

PICKUP DRIVE CONTROLLER FOR OPTICAL DISC DRIVE

TECHNICAL FIELD

The present invention relates to a controller for driving a pickup of an optical disk drive as typified by a CD-ROM drive and, more particularly, to a pickup drive controller which performs a seek (fast-forward/fast-rewind) followed by a read, with no waste, to improve the stability of the read.

BACKGROUND ART

In recent years, optical disk drives have rapidly became standard-equipment on personal computers, and they have become an indispensable feature of personal computers along with hard disk drives. While CD-ROM drives have initially made up the majority of optical disk drives, DVD-ROM drives having a larger capacity than that of CD-ROM drives or recordable or rewritable CD-R/CD-RW drives which are standard-equipment on personal computers these days, and further, DVD-R or DVD-RAM drives have appeared on the market. Thus, there are no bounds to enhancement in performance and function of optical disk drives.

An example of an optical disk drive is illustrated in FIG. 1. In the figure, numeral 11 denotes an optical disk (hereinafter, merely referred to as a disk), numeral 12 denotes a spindle motor for rotating the disk 11, numeral 13 denotes a pickup for reading data on the disk 11, numeral 14 denotes a lens which focuses a reflected light beam from the disk 11 onto the pickup 13, numeral 15 denotes a feed which movably supports the pickup 13, numeral 16 denotes a feed motor which drives the feed 15 to move the pickup 13, numeral 17 denotes a driver IC which performs control for driving the spindle motor 12, the pickup 13, the feed motor 16, and a digital signal processor IC 19, numeral 18 denotes an analog front end IC which processes an RF signal from the pickup 13, numeral 19 denotes a digital signal processor IC which processes a digital signal from the analog front end IC 18, numeral 20 denotes a decoder IC for decoding the digital signal outputted from the digital signal processor IC 19, numeral 21 denotes a CPU which controls the driver IC 17, the analog front end IC 18, the digital signal processor IC 19, and the decoder IC 20 of the optical disk drive, and numeral 22 denotes a host, such as a personal computer body or the like, which issues an instruction to the optical disk drive.

Next, the operation will be described. The disk 11 is rotationally driven at a constant linear velocity or a constant angular velocity by the spindle motor 12. To the rotating disk 11, the pickup 13 moves from the inner circumference toward the outer circumference of the disk in a radial direction, and applies a laser beam onto the disk surface to read data thereon from a change of its reflected light. Data called pits, which are generally referred to as tracks, are spirally recorded on the disk surface, and in order to read the data accurately, the pickup 13 drives the lens 14, which is supported by a wire in a housing in the pickup 13, vertically to the disk surface, and focuses the laser beam onto the disk surface. Further, the pickup 13 detects a deviation of the laser beam from the center of the track by detecting a change of the reflected laser beam from the disk surface, and drives the lens 14 horizontally to the disk surface in a radial direction to perform tracking control so that the laser beam is positioned in the center of the data (track). The lens 14 is subjected to focus servo control and tracking servo control with the disk 11, and the pickup 13 reads the data from the disk surface and sends them to the analog front end IC 18. Thereafter, the reproduced data are transferred to the host 22 via the digital signal processor IC 19 and the decoder IC 20.

Since data are spirally recorded on the disk surface as described above, the pickup 13 has to move from the inner circumference toward the outer circumference with the passage of time. There are two methods of moving the pickup 13, one is a method of moving the lens 14 in the housing of the pickup 13 and the other is a method of moving the feed 15 to which the pickup 13 is fixed.

There is generally employed a method of initially moving the lens 14 to follow the track, and then moving the feed 15 to return the lens 14 to the center of the housing when the lens 14 is moved by a predetermined distance or more from the center of the housing. Meanwhile, when data at an arbitrary position on the disk surface are read according to an instruction from the exterior (such as the host), a seek operation is performed. The seek operation is fast-forward or fast-rewind, in which the number of tracks from the present position to a target position is obtained by calculation, and the pickup 13 is moved by the number of tracks at high speed.

There are two methods of moving the pickup 13 in the seek operation. A seek which moves the feed 15 to carry the pickup 13 to a target position is generally referred to as a feed seek, which is employed for a move of a relatively long distance. On the other hand, a seek which does not move the feed 15, but moves the lens 14 in the housing of the pickup 13 so that the lens 14 reaches a target position, is generally referred to as a kick seek, which is employed for a move of a relatively short distance. The seek operation is performed by combining these two kinds of seeks.

Since, as shown in FIG. 2, a lens 24 is supported by wires 25 and 26 in a pickup 23 in the above-described optical disk drive, it is extremely vulnerable to external vibrations or the like. That is, since the above-described feed seek is, so to speak, an external vibration for the pickup, too fierce an acceleration or deceleration of the feed movement makes a lens 34 deviate from the center in a pickup 33 when the feed seek is ended, as shown in FIGS. 3(a) and 3(b). FIG. 3(a) illustrates a case where the lens 34 is shifted toward the outer circumference in the pickup 33 due to a seek toward the inner circumference, and FIG. 3(b) illustrates a case where the lens 34 is shifted toward the inner circumference in the pickup 33 due to a seek toward the outer circumference.

Another problem is that the feed inertially continues moving even after the feed seek is ended, resulting in an offset of the lens. FIGS. 4(a) and 4(b) illustrate a positional alteration of the lens in the pickup after the feed seek. FIG. 4(a) shows the state when the feed seek has just ended. At this point in time, the lens 44 is located in the center of the pickup 43. However, actually, the feed continues moving inertially, and the lens 44 may shift by the time of the kick seek as shown in FIG. 4(b). This results in the same problem as the above-described offset of the lens due to too fierce acceleration or deceleration of the feed movement.

Next, what kind of adverse effect the offset of the lens has on the servo control will be described with reference to FIG. 5. Usually, the lens is located at a lens position 52, that is, the center of the pickup, and refracts a light from a laser 54 to focus it onto the surface of a disk 51. The lens has a function of returning a reflected light from the disk 51 to a photoreceptor unit 55 of the pickup. However, when the lens is shifted and located at a lens position 53, the reflected light from the laser 54 is not incident on the photoreceptor unit 55 as shown by a dotted line. Therefore, accurate data reading is disturbed, and further, the tracking servo becomes unstable when the lens is shifted because the tracking servo generates a positional signal from the reflected light of the disk.

When an instruction of read from an arbitrary position is issued by the host 22 shown in FIG. 1, it is ideal that a seek position 63 is set just before a read start position (target position) 62 as the arbitrary position as shown in FIG. 6. The distance between the seek position 63 and the read start position 62 is shorter than the distance of one sector 61. Actually, however, a lens offset may occur by the seek, as described above, and therefore, a seek position 73 is set several sectors 77 before a read start position 72 (at the inner circumference of the disk), and play tracing is made to the read start position 72 at the same tracing speed as a speed of normal playback to reduce a lens offset 74 from a lens offset 75 at seek end to a lens offset 76 at read start, as shown in FIG. 7.

However, the situation where the seek position is several sectors 77 before the read start position 72 is the same in any seek, and thus, additional access time is required for the time of play tracing for the several sectors 77. Further, even when the seek position is set as described above, if the amount of generated lens offset is extremely large, the lens offset is not removed by the time of read start, and a read error may occur.

The present invention is made to solve the above-mentioned problems and has for its object to provide a controller for driving a pickup of an optical disk drive, which can perform a read after stabilizing movement of a lens.

SUMMARY OF THE INVENTION

In order to solve the above-mentioned problems, according to a first aspect of the present invention, a controller for driving a pickup of an optical disk drive, comprises: a lens offset measuring means for measuring the amount of an offset of a lens from the center of the lens in a pickup, which offset occurs at a seek of the pickup; and a seek position setting means for setting a seek position where a seek toward a target position of the pickup is ended, in a pickup driving means, on the basis of two parameters, the amount of lens offset measured by the lens offset measuring means and the number of seek tracks to seek.

Since the invention of the first aspect is constructed as described above, when a lens offset before a seek is small or when a lens offset is seldom generated at a seek, a seek position is made close to a target position, whereby an optimum seek position at which the lens offset is canceled can be set with no waste, resulting in an improvement in access time at read.

Accordingly, as described above, when a lens offset before a seek is small or when a lens offset is seldom generated at a seek, a seek position is made close to a target position, whereby an optimum seek position at which the lens offset is canceled to the target position can be set with no waste. Therefore, access time at read is improved, and reliability of read is improved.

According to a second aspect of the present invention, in a controller for driving a pickup of an optical disk drive as defined in the first aspect, the lens offset measuring means also measures the direction of the lens offset, in addition to the amount of the lens offset from the center of the lens in the pickup, which offset occurs at the seek of the pickup; and the seek position setting means also uses two parameters, the lens offset direction and the seek direction, as parameters for determining the seek position.

Since the invention of the second aspect is constructed as described above, even when a certain degree of lens offset occurs, a seek position can be made close to a read start position depending on the offset direction and the direction of the next seek, whereby an optimum seek position at which the lens offset is canceled can be set with no waste, resulting in a further improvement in access time at read.

Accordingly, as described above, even when a certain degree of lens offset occurs, a seek position can be made close to a read start position depending on the offset direction and the direction of the next seek, whereby an optimum seek position at which the lens offset is canceled can be set with no waste, resulting in a further improvement in access time at read.

According to a third aspect of the present invention, in a controller for driving a pickup of an optical disk drive as defined in the first aspect, the seek position setting means changes a seek position for a target position according to a rotation speed of a disk.

Since the invention of the third aspect is constructed as described above, when a lens offset is canceled, a seek position can be made closer to a read start position when the rotation speed is low rather than when it is high, whereby an optimum seek position according to the rotation speed can be set with no waste, resulting in a further improvement in access time at read.

Therefore, as described above, at a point of time where a lens offset is canceled, a seek position can be made closer to a read start position when the rotation speed is low rather than when it is high, whereby an optimum seek position according to the rotation speed can be set with no waste, resulting in a further improvement in access time at read.

According to a fourth aspect of the present invention, a controller for driving a pickup of an optical disk drive comprises: a lens offset measuring means for measuring the amount and direction of an offset of a lens from the center of the lens in a pickup at seek end, and storing the amount and direction; and a seek position setting means for comparing an offset amount and an offset direction just before a seek with the offset amount and the offset direction stored in the lens offset measuring means when the number of seek tracks of a next seek is smaller than a predetermined value, thereby calculating the movement of a feed just before the seek, which feed movably supports the pickup and, on the basis of the calculation result, setting, in a pickup driving means, a seek position where the seek toward the target position of the pickup is to be ended.

Since the invention of the fourth aspect is constructed as described above, a lens offset which is caused by the movement of the feed that is not settled is estimated, and an optimum seek position where the lens offset is canceled can be determined, resulting in a stable read operation.

Therefore, as described above, a lens offset which is caused by the movement of the feed that is not settled can be estimated, and an optimum seek position where the lens offset is canceled can be determined, thereby realizing a stable read operation.

According to a fifth aspect of the present invention, in a controller for driving a pickup of an optical disk drive as defined in the fourth aspect, the seek position setting means changes the seek position for the target position according to a rotation speed of a disk.

Since the invention of the fifth aspect is constructed as described above, when a lens offset is canceled, a seek position can be made closer to a read start position when the rotation speed is low rather than when it is high, whereby an optimum seek position according to the rotation speed can be set with no waste, resulting in a further improvement in access time at read.

Therefore, as described above, at a point of time where a lens offset is canceled, a seek position can be made closer to a read start position when the rotation speed is low rather than when it is high, whereby an optimum seek position according to the rotation speed can be set with no waste, resulting in a further improvement in access time at read.

According to a sixth aspect of the present invention, in a controller for driving a pickup of an optical disk drive as defined in the first and fourth aspects, the seek position setting means sets a seek position for a target position at least one sector before the target position.

Since the invention of the sixth aspect is constructed as described above, unnecessary vibrations of the lens just after the seek are absorbed in a sector just before read, resulting in a stable read operation.

Therefore, as described above, unnecessary vibrations of the lens just after the seek are absorbed in a sector just before read, thereby realizing a stable read operation.

According to a seventh aspect of the present invention, a controller for driving a pickup of an optical disk drive comprises: a lens offset measuring means for measuring the amount of an offset of a lens from the center of the lens in a pickup; and a seek position setting means for setting, in a pickup driving means, a seek position where a seek toward a target position of the pickup is to be ended, as well as a seek position at kickback, so that kickback for seeking the pickup in an inverse direction of the original seek is performed until the amount of offset at seek end becomes smaller than a predetermined value.

Since the invention of the seventh aspect is constructed as described above, a lens offset is always canceled at read, resulting in stable read. Further, a seek position can be set just before a read start position, whereby the processing can promptly shift from seek to read when the offset is small, resulting in an improvement in access time.

Therefore, as described above, the amount of lens offset is measured when seek is ended, and not read, but kickback is performed until this value becomes smaller than a prescribed value, whereby a lens offset is always canceled at read, resulting in stable read. Further, a seek position can be set just before a read start position, whereby the processing can promptly shift from seek to read when the offset is small, resulting in an improvement in access time.

According to an eighth aspect of the present invention, in a controller for driving a pickup of an optical disk drive as defined in the seventh aspect, the seek position setting means employs the amount of an offset of a lens from the center of the lens in the pickup at a point in time where a read error occurs, as a value to be compared with the amount of offset at seek end.

Since the invention of the eighth aspect is constructed as described above, a maximum offset amount at which no error occurs can be obtained while an offset amount at which a read error occurs is learned in an actual operation. Therefore, unnecessary kickback is dispensed with, resulting in stable read and improved access time.

Therefore, as described above, a maximum offset amount at which no error occurs can be obtained while an offset amount at which a read error occurs is learned in an actual operation, whereby unnecessary kickback is dispensed with, resulting in stable read and improved access time.

According to a ninth aspect of the present invention, in a controller for driving a pickup of an optical disk drive as defined in the eighth aspect, the seek position setting means has a limiter for setting a lower limit so that the value to be compared with the amount of offset at seek end does not become smaller than a predetermined value.

Since the invention of the ninth aspect is constructed as described above, read is performed actively when it can be performed, and therefore, unnecessary kickback is dispensed with to improve access time.

Therefore, read is performed actively when it can be performed, whereby unnecessary kickback is dispensed with to improve access time.

BRIEF DESCRIPTION OF DRAWINGS

FIG. 3(a) shows a case where the lens is shifted toward the outer circumference in the pickup due to a seek toward the inner circumference, while FIG. 3(b) shows a case where the lens is shifted toward the inner circumference in the pickup due to a seek toward the outer circumference.

FIG. 4(a) shows positional movement just after a feed seek is ended, while FIG. 4(b) shows an offset of the lens when a kick seek is performed.

DETAILED DESCRIPTION OF THE INVENTION

Figure 1:
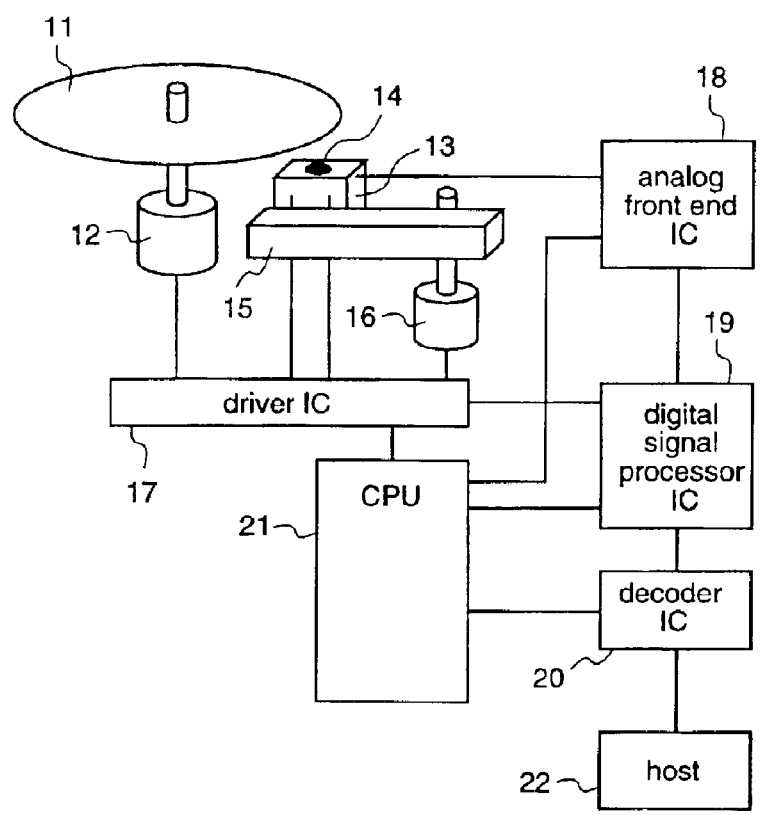
FIG. 1 is a block diagram illustrating an optical disk drive according to first, second, and third embodiments of the present invention, as well as a conventional example.
Figure 2:
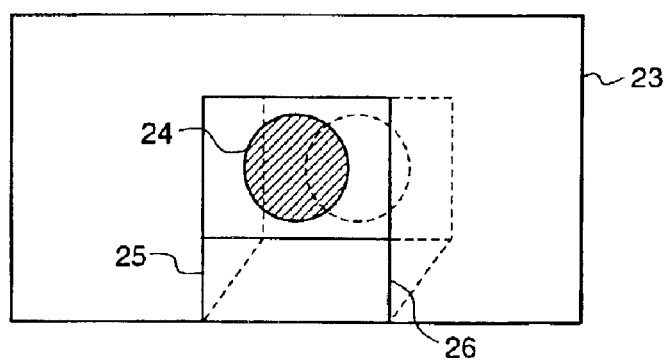
FIG. 2 is a diagram illustrating a construction of a pickup of the optical disk drive shown in FIG. 1.
Figure 3A:
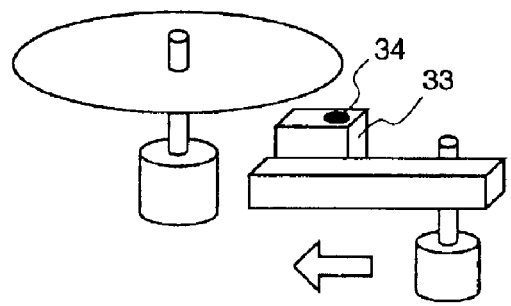
FIGS. 3(a) and 3(b) are diagrams illustrating a state where a lens of the optical disk drive shown in FIG. 1 is shifted.
Figure 3B:
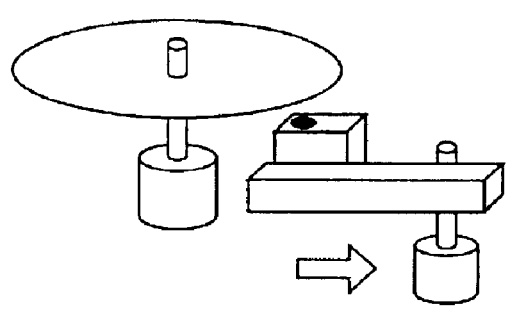
Figure 4A:
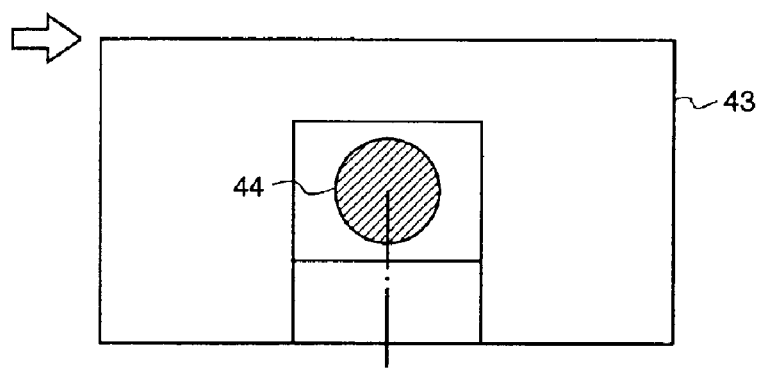
FIGS. 4(a) and 4(b) are diagrams illustrating a state where a feed of the optical disk drive shown in FIG. 1 is shifted.
Figure 4B:
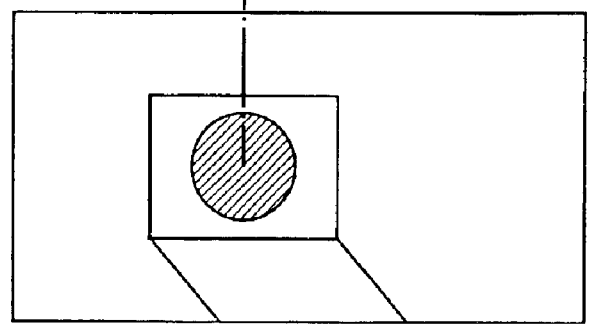
Figure 5:
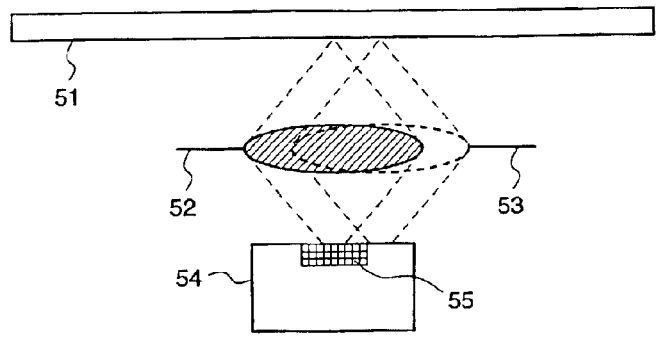
FIG. 5 is a diagram illustrating a state where the optical disk drive shown in FIG. 1 receives a reflected light.
Figure 6:
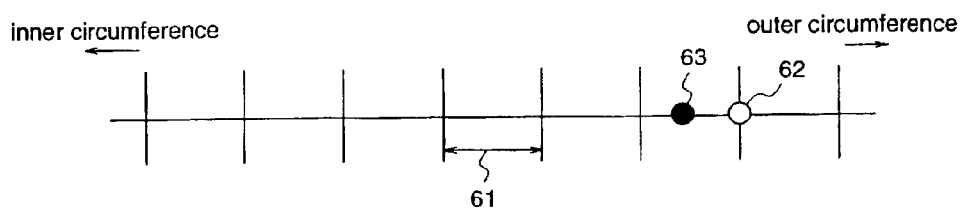
FIG. 6 is a diagram illustrating a seek position of the optical disk drive shown in FIG. 1.
Figure 7:
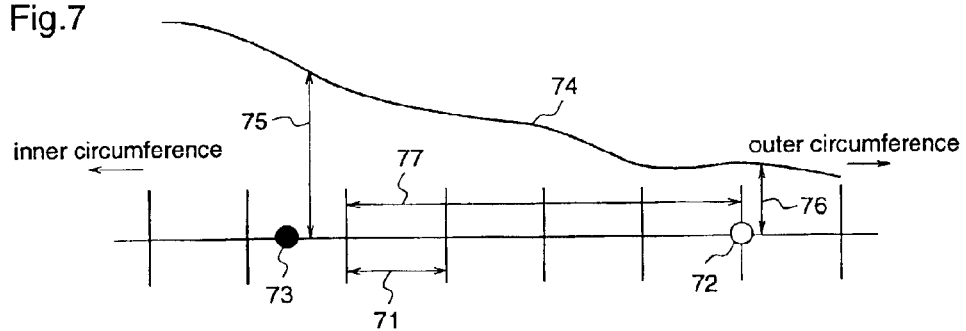
FIG. 7 is a diagram illustrating a seek position offset of the optical disk drive shown in FIG. 1.

Hereinafter, an optical disk drive according to embodiments of the present invention will be specifically described with reference to the drawing.

(Embodiment 1)

A first embodiment which corresponds to an optical disk drive as defined in the first through third aspects of the present invention will be described with reference to FIGS. 1 and 8 to 13.

In this first embodiment, when a lens shift before a seek is insignificant and a seek is carried out in units of several seeks that hardly cause lens shift, the number of seeks is set at minimum. At other times, the number of seeks is determined on the basis of the amount of lens shift before a seek and the number of seeks. Thereby, generation of unnecessary seeks is avoided to improve access time.

In a block diagram of FIG. 1, the amount of offset of a lens 14 is inputted to an A/D converter terminal of a CPU 21 of the optical disk drive from a pickup 13 through an analog front end IC 18. Therefore, the CPU 21 performs A/D conversion of an output signal from a photoreceptor unit of the pickup 13 by a built-in A/D converter and detects an offset, thereby obtaining the offset amount and offset direction of the lens. Thereby, a lens offset measuring means (not shown) which measures the amount of offset from the center of the lens in the pickup, which occurs at a seek of the pickup, is constructed.

To make the first embodiment correspond to the invention according to the first aspect, when a seek is to be performed first according to a read instruction from the host 22, the CPU 21 measures an offset of the lens and determines a seek position by the following formula (1):

$$\text{SeekPos} = \text{ReadPos} - (|\text{offset}|/\alpha + T/\beta) \quad (1)$$

wherein, SeekPos: seek position (sector)

ReadPos: read start position (sector)

offset: amount of lens offset

T: number of seeks

α: factor

β: factor

The CPU 21 calculates the formula (1), thereby constructing a seek position setting means (not shown) which sets a seek position where a seek toward a target position of the pickup is ended, in a driver IC 17 as a pickup driving means, on the basis of two parameters, i.e., the amount of lens offset measured by the lens offset measuring means, and the number of seek tracks to seek.

Generally, in a seek, as the number of seeks becomes larger, the distance to move the pickup increases, resulting in a risk of increasing the lens offset. When the number of seeks is small, a change of the lens offset can be neglected. That is, since the lens offset caused by a seek correlates with the number of seeks, an amount of offset to be generated after a seek is estimated from the number of seeks and is incorporated in the formula (1).

Here, an actual driving pattern on the basis of formula (1) will be described.

Figure 8:
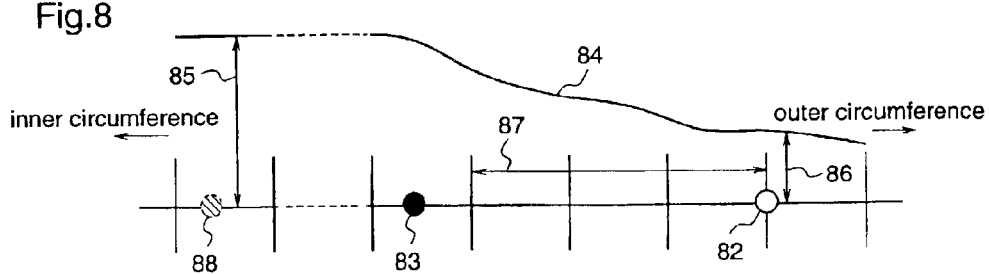
FIG. 8 is a diagram illustrating a seek position offset of the optical disk drive according to the first embodiment of the present invention.

First of all, the number-of-seeks T is set to a sufficiently small value at which no offset is generated. In FIG. 8, which illustrates a case where the lens offset before a seek is large, a seek position 83 is set a number-of-sectors 87 before a read start position 82, according to the amount of a lens offset 85 at a before-seek position 88. Although the lens offset just after the seek is the same as that before the seek because this number of seeks is a sufficiently small value, a lens offset 84 can be reduced to a lens offset 86 at the read start position 82 by performing a play tracing for the-number-of-sectors 87 after the seek.

Figure 9:
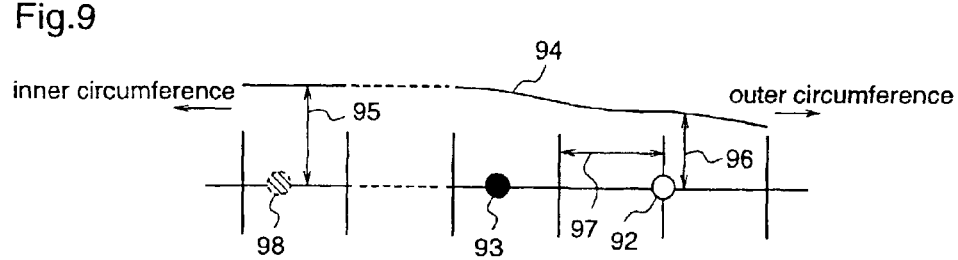
FIG. 9 is a diagram illustrating a seek position offset of the optical disk drive according to the first embodiment of the present invention.

On the other hand, in FIG. 9, which illustrates a case where a lens offset 95 at a before-seek position 98 is small, a seek position 93 is set a number-of-sectors 97 before a read start position 92. The number-of-sectors 97 is smaller in value than the number-of-sectors 87. Although the seek position 93 is located just before the read start position 92, a lens offset 96 at the read start position 92 is sufficiently small in value since a lens offset 94 is originally small.

In the conventional optical disk drive, the sector difference 87 between the read start position 82 and the seek position 83 in FIG. 8 is always set constant regardless of the lens offset value. In the present invention, however, since the seek position is determined based on formula (1), the sector difference 87 varies according to the amount of lens offset and the number of seeks, such that the sector difference increases as the amount of lens offset and the number of seeks become larger.

Further, when the lens offset before a seek is small, as shown in FIG. 9, the sector difference 97 between the read start position 92 and the seek position 93 is decreased so that unnecessary play tracing time is saved, thereby improving access time.

Figure 10:
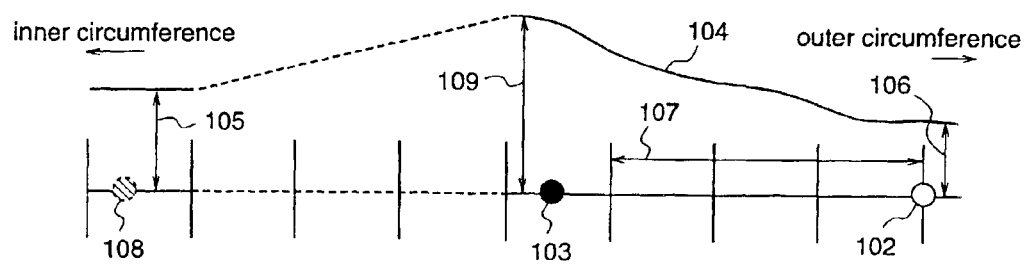
FIG. 10 is a diagram illustrating a seek position offset of the optical disk drive according to the first embodiment of the present invention.
Figure 11:
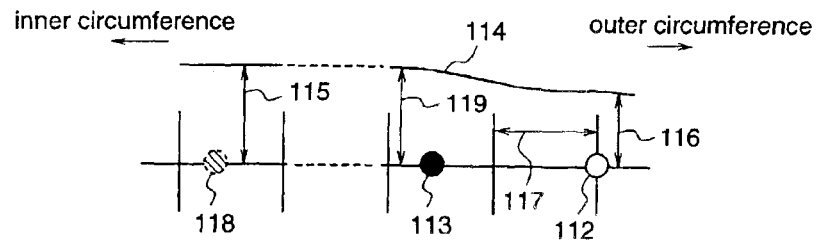
FIG. 11 is a diagram illustrating a seek position offset of the optical disk drive according to the first embodiment of the present invention.

Next, a driving pattern in which the number of seeks is changed with a lens offset value before a seek being an arbitrary value will be described with reference to FIGS. 10 and 11. In FIG. 10, which illustrates a case where the number-of-seeks T is sufficiently large so that a lens offset is generated, a seek position 103 is set a number-of-sectors 107 before a read start position 102 according to the number of seeks T. In this case, a lens offset 109 just after a seek is increased as compared with an offset 105 at a before-seek position 108 because of the large number of seeks. However, by performing a play tracing for the number-of-sectors 107 after the seek, a lens offset 104 can be reduced to a lens offset 106 at the read start position 102. In FIG. 11, which illustrates a case where the number of seeks T is sufficiently small so that a lens offset is not generated, a seek position 113 is set a number-of-sectors 117 before a read start position 112 according to the numbed of seeks T. The number-of-sectors 117 is smaller in value than the number-of-sectors 107. Although the seek position 113 is located just before the read start position 112, a lens offset 116 at the read start position 112 is sufficiently small in value since a lens offset 115 at a before-seek position 118 is equal to a lens offset 119 at the seek position 113 and no offset is generated due to the seek between them.

In the conventional optical disk drive, the sector difference 107 between the read start position 102 and the seek position 103 in FIG. 10 is always constant regardless of the number of seeks. In the present invention, however, since the seek position is determined based on formula (1), the sector difference 107 varies according to the amount of lens offset and the number of seeks, such that the sector difference increases as the amount of lens offset and the number of seeks become larger.

Further, when the number of seeks is small, as shown in FIG. 11, the sector difference 117 between the read start position 112 and the seek position 113 is further decreased so that unnecessary play tracing time is saved, thereby improving access time.

As described above, an offset amount from the center of the lens in the pickup is measured, and a seek position is determined according to two parameters, i.e., the amount of lens offset and the number of seek tracks, when a seek which is followed by a read is carried out. Therefore, when the lens offset before the seek is small or when a seek which hardly causes a lens offset is carried out, the seek position is brought close to the read start position, whereby an optimum seek position at which the lens offset is canceled can be set with no waste, resulting in an improvement in access time at read.

In order to make the first embodiment correspond to the invention according to the second aspect, when a seek is to be performed first according to a read instruction from the host 22, the CPU 21 which constructs the lens offset measuring means measures the offset amount and the offset direction of the lens 14, and determines a seek position by the following formula (2):

$$SeekPos = ReadPos - (|offset|/\alpha + T/\beta) \qquad (2)$$

wherein, SeekPos: seek position (sector)
ReadPos: read start position (sector)
offset: amount of lens offset (toward inner circumference: +, toward outer circumference: −)
T: number of seeks (toward inner circumference: −, toward outer circumference: +)
α: factor
β: factor The CPU 21 which constructs the seek position setting means calculates formula (2) to determine a seek position by using, as parameters, the lens offset direction and the seek direction as well as the amount of offset of the lens 14 and the number of seek tracks to seek.

Figure 12:
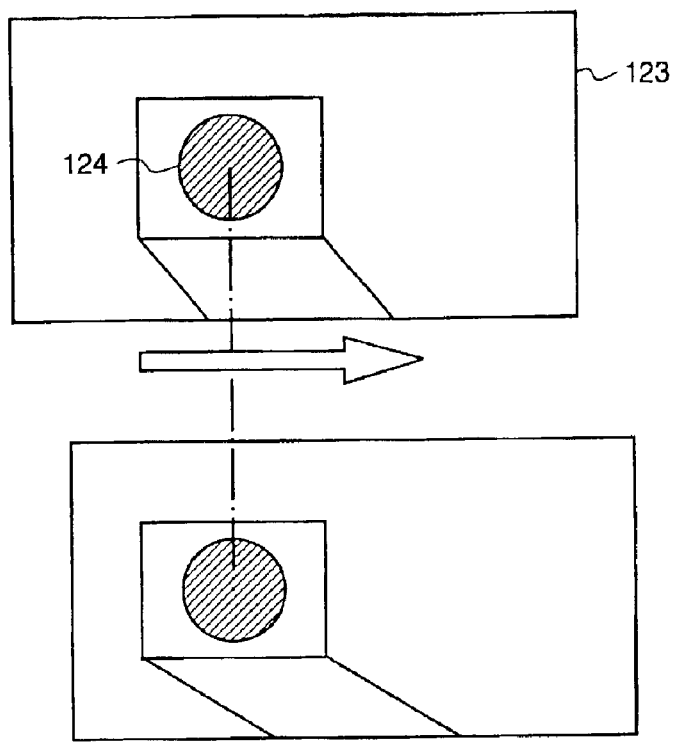
FIG. 12 is a diagram illustrating a lens offset of the optical disk drive according to the first embodiment of the present invention.

FIG. 12 is a diagram illustrating a case where a lens 124, which is offset toward the inner circumference in a pickup 123, seeks toward the outer circumference. Because the direction of this seek is one which increases the lens offset, the seek position obtained by formula (2) is the same as the position calculated by formula (1) which corresponds to the first aspect.

Figure 13:
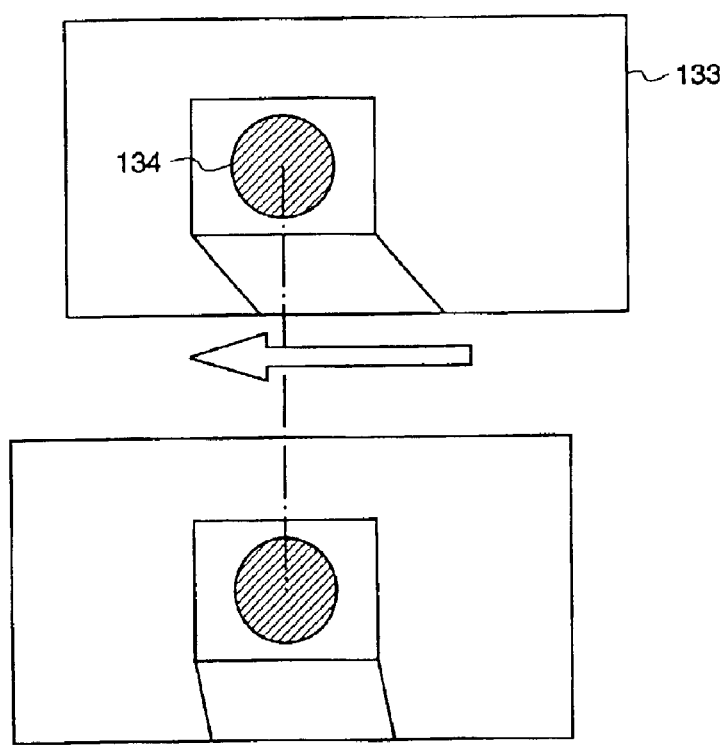
FIG. 13 is a diagram illustrating a lens offset of the optical disk drive according to the first embodiment of the present invention.

On the contrary, FIG. 13 is a diagram illustrating a case where a lens 134, which is offset toward the inner circumference in a pickup 133, seeks toward the inner circumference furthermore. Because, in this case, the direction of this seek is one which cancels a lens offset, the seek position can be brought closer to the read start position than the calculated position in the case of Claim 1. Therefore, in order to reflect this point, in formula (2), the seek direction and the lens offset direction are also considered as parameters, and the seek position can be made closer to the read start position as compared with the first aspect when the lens offset direction is the same as the seek direction. Thereby, access time can be further improved.

As described above, an offset amount from the center of the lens in the pickup is measured when performing a seek which is followed by a read, and a seek position is determined according to four parameters, i.e., the amount of lens offset, the direction of lens offset, the number of seek tracks, and the seek direction. Therefore, even when a certain degree of lens offset is generated, the seek position can be made close to the read start position depending on the direction of offset and the direction of the next seek, whereby an optimum seek position at which the lens offset is canceled can be set with no waste, resulting in a further improvement in access time at the read.

Next, in order to make the first embodiment correspond to the invention according to the third aspect, a seek position is set by the following formula (3) which is based on formula (1) for obtaining the seek position according to Claim 1.

$$SeekPos = ReadPos - (R/\gamma)(|offset|/\alpha + T/\beta) \qquad (3)$$

wherein, R: number of rotation
γ: factor

The CPU 21, which constructs the seek position setting means, calculates formula (3) so as to change the seek position with respect to a target position also by the rotation speed of the disk.

The seek position with respect to the read start position is changed according to the rotation speed of the disk by employing formula (3), whereby the actual time for a play tracing until the convergence of a lens offset from the seek position to the read start position becomes constant regardless of the rotation speed of the disk. Therefore, unnecessary play tracing time can be reduced when the rotation speed is low, resulting in a further improvement in access time.

As described above, since the seek position with respect to the read start position is changed according to the rotational speed of the disk, when canceling the lens offset, the seek position can be made closer to the read start position when the rotation speed is low rather than when the rotation speed is high, whereby an optimum seek position according to the rotation speed can be set with no waste, resulting in a further improvement in access time at a read.

(Embodiment 2)

Figure 14:
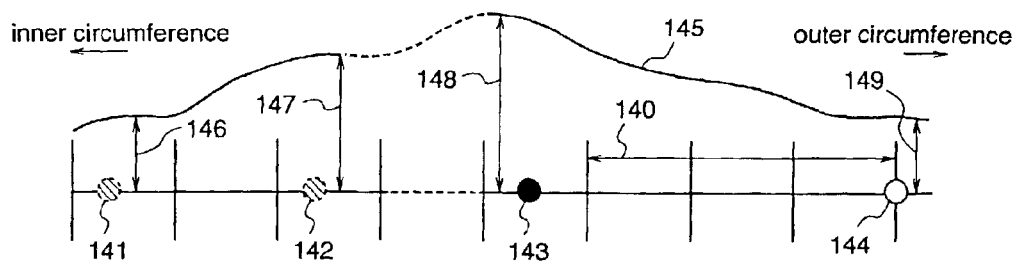
FIG. 14 is a diagram illustrating a seek position offset of the optical disk drive according to the second embodiment of the present invention.

Next, a second embodiment which corresponds to an optical disk drive as defined in the fourth through sixth aspects of the present invention will be described with reference to FIGS. 1 and 14. The same constituents as those described in the first embodiment will be denoted by the same reference numerals, and description therefor will be omitted.

In this second embodiment, a feed position is calculated on the basis of a seek position when the previous seek is ended and a seek position when the next seek is started, and a further seek position is set before a read start position when the feed is moved by a prescribed value or more, thereby canceling an offset of the feed due to the continuous movement of the feed to enhance reading performance.

In order to make the second embodiment correspond to the invention according to the fourth aspect, when a seek is to be performed first according to a read instruction from the host 22 shown in FIG. 1, the CPU 21 compares the amount of lens offset which is measured when the previous seek is ended with the amount of lens offset which is measured just before a seek at this time to obtain the speed of the feed which inertially continues moving. A seek position is determined by the following formula (4) employing this speed.

$$SeekPos = ReadPos - |offset1 - offset2|/\alpha \qquad (4)$$

wherein, SeekPos: seek position (sector)
ReadPos: read start position (sector)
Offset1: amount of lens offset when previous seek is ended
Offset2: amount of lens offset when this-time seek is started
α: factor Here, since the number of seek tracks is under a predetermined value at which no lens offset occurs, correction by the number of seeks is neglected.

The CPU 21, which constructs a seek position setting means, calculates formula (4) to compare an offset amount and an offset direction just before a seek with those of the previous seek when the number of seek tracks of the next seek is smaller than a predetermined value, whereby the CPU 21 calculates the movement of the feed just before the seek, which feed movably supports the pickup, and then the CPU 21 sets a seek position where the seek toward a target position of the pickup is ended, in the driver IC 17 as a pickup driving means, on the basis of the calculation result.

Next, an actual driving pattern on the basis of formula (4) will be described. FIG. 14 shows a case where the feed has a speed in the direction toward the outer circumference at seek start. In this case, a lens offset 146 at a previous-seek position 141 is increased to a lens offset 147 at a this-time-seek start 142, which indicates that the feed has a speed in the direction toward the outer circumference. Therefore, a seek position 143 is set a number-of-sectors 140 before a read start position 144 according to formula (4). Thereby, a lens offset 145 is sufficiently reduced from a lens offset 148 at a seek position 143 to a lens offset 149 at a read start position 144, whereby the read can be carried out with stability.

On the contrary, when the feed does not have a speed, since the seek position is set just before the read start position according to the formula (4), unnecessary play tracing is not performed, thereby improving access time.

As described above, the offset amount and offset direction of the lens from the center in the pickup are measured and stored when the seek is ended and, when the number of seek tracks of a seek that is followed by the next read is smaller than an arbitrary value, the stored offset amount and direction are compared with an offset amount and an offset direction just before the seek to calculate the movement of the feed just before the seek, whereby a seek position is determined. Therefore, a lens offset generated because the movement of the feed is not settled is estimated, and an optimum seek position where the lens offset is canceled can be determined, resulting in a stable read operation.

Next, in order to make the second embodiment correspond to the invention according to the fifth aspect, a seek position is set by the following formula (5) which is based on formula (4) for obtaining the seek position according to the fourth aspect.

$$\text{SeekPos}=\text{ReadPos}-(R/\gamma)(|\text{offset1}-\text{offset2}|/\alpha) \qquad (5)$$

wherein, R: number of revolutions

γ: factor

The CPU 21, which constructs the seek position setting means, calculates formula (5) to change the seek position for a target position on the basis of the rotation speed of the disk.

The seek position is changed according to the rotation speed of the disk by formula (5), whereby the actual time for a play tracing until the convergence of a lens offset from the seek position to the read start position becomes constant regardless of the rotation speed of the disk. Therefore, unnecessary play tracing time can be reduced when the rotation speed is low, resulting in a further improvement in access time.

As described above, since the seek position for the read start position is changed according to the rotation speed of the disk, when the lens offset is to be canceled, the seek position can be made closer to the read start position when the rotation speed is low rather than when it is high, whereby an optimum seek position according to the rotation speed can be set with no waste, resulting in a further improvement in access time at read.

Next, in order to make the second embodiment correspond to the invention according to the sixth aspect, when the relationship SeekPos=ReadPos holds in formulas (1) and (4) for obtaining the seek positions according to the first and fourth aspects, the following processing is performed:

$$\text{SeekPos}=\text{ReadPos}-\alpha \qquad (6)$$

wherein, α is a variable which satisfies $\alpha \geq 1$.

The CPU 21, which constructs the seek position setting means, calculates formula (6) to set a seek position corresponding to a target position at least one sector before a read start position.

Therefore, the seek position can be set at least one sector before the read start position, and at least one sector is retained by the time of read start after the seek, whereby unnecessary vibrations of a lens after the seek are suppressed to realize a stable read operation.

As described above, since the seek position for the read start position is set at least one sector before the read start position, unnecessary vibrations of the lens just after the seek are absorbed in one sector just before read, whereby a stable read operation is realized.

(Embodiment 3)

A third embodiment which corresponds to an optical disk drive as defined in the seventh through ninth aspects of the present invention will be described with reference to FIGS. 1, 15, 16, 17 and 18.

In this third embodiment, a seek position is set just before a read start position, and the processing shifts to a read when a lens shift after the seek is at a level having no problem. When a lens shift occurs, a kickback of one track is performed and continued until the lens shift is settled. Therefore, the access time is improved because the processing promptly shifts to the read when no lens shift occurs. On the other hand, when a lens shift occurs, this is suppressed by kickback to improve reading performance.

In the block diagram of FIG. 1, the amount of offset of the lens 14 is inputted to the A/D converter terminal of the CPU 21 from the pickup 13 via the analog front end IC 18. Therefore, the CPU 21 subjects an output signal from the photoreceptor unit of the pickup 13 to A/D conversion using a built-in A/D converter, and detects an offset, thereby obtaining the offset amount and offset direction of the lens.

Figure 15:
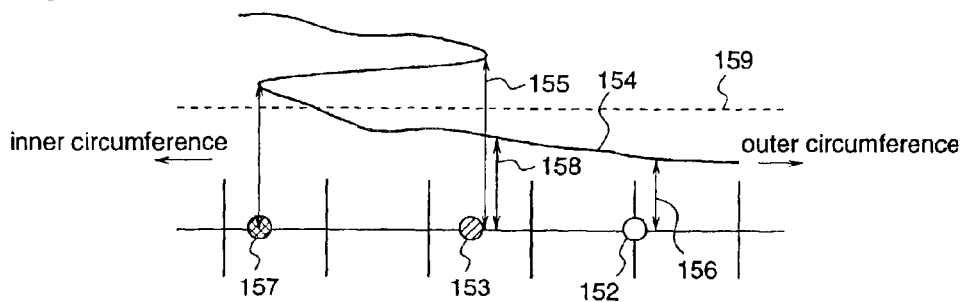
FIG. 15 is a diagram illustrating a kickback operation of the optical disk drive according to the third embodiment of the present invention.

In order to make the third embodiment correspond to the invention according to the seventh aspect, when a seek is to be performed first according to a read instruction from the host 22, the CPU 21 measures an offset of the lens at seek end. In FIG. 15, when a lens offset amount 155 at a seek end position 153 is larger than a threshold offset amount 159, a seek is performed for a track toward the inner circumference. This operation is called kickback, by which the seek position shifts to a seek end position 157. Then, it is confirmed that a lens offset amount 158 when the position 157 is shifted to the position 153 by play tracing is smaller than the threshold offset value 159, and read is performed from a read start position 152. A lens offset amount 156 at the read start position 152 is smaller than the lens offset 158 at the seek end position 153. When the lens offset amount 158 at the position 153 is larger than the threshold offset value 159, kickback is performed again and repeated until the lens offset amount 158 becomes smaller than the threshold offset value 159.

The CPU 21, which constructs a seek position setting means, performs the above-described processing, whereby the CPU 21 sets a seek position, where the seek toward a target position of the pickup is ended, and a seek position at kickback in the driver IC 17 as a pickup driving means so as to perform kickback for seeking the pickup in an inverse direction of the original seek until the offset amount at seek end becomes smaller than a prescribed value.

Thereby, the processing shifts to read after a lens offset amount 154 is converged, resulting in a stable read operation.

Figure 16:
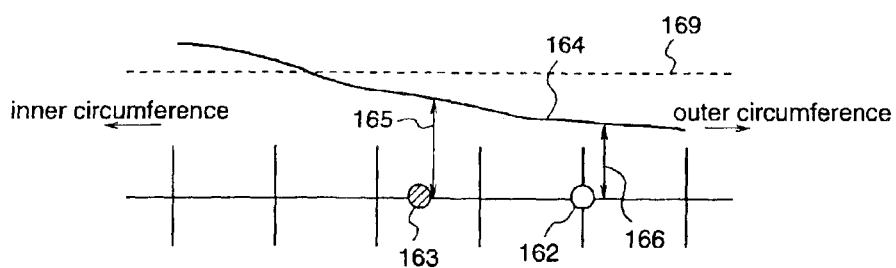
FIG. 16 is a diagram illustrating a seek operation of the optical disk drive according to the third embodiment of the present invention.

FIG. 16 is a diagram illustrating a case where a lens offset amount 165 at a seek end position 163 is smaller than an threshold offset value 169 from the beginning. In this case, there is no need to perform kickback for reducing a lens offset 164, and read a is performed from a read start position 162. A lens offset 166 at the read start position 162 is smaller than the lens offset at the seek end position 163. In this way, since the lens offset just after the seek is monitored, the seek position can be set just before the read start position, resulting in a reduction in seek time.

As described above, the amount of lens offset is measured when the seek followed by the read is ended, and not read, but kickback is performed until this value becomes lower than an arbitrary value, whereby the lens offset is always canceled at the time of read, resulting in a stable read. Further, since the seek position can be set just before the read start position, the processing can promptly shift from the seek to read when the offset is small, resulting in an improvement in access time.

Next, in order to make the third embodiment correspond to the invention according to the eighth aspect, the above-described arbitrary offset amount is changed in the actual operation. That is, the CPU 21, which constructs the seek position setting means, employs the value of the amount of lens offset from the center in the pickup at a point of time where a read error occurs, as a value to be compared with the offset amount at seek end.

Figure 17:
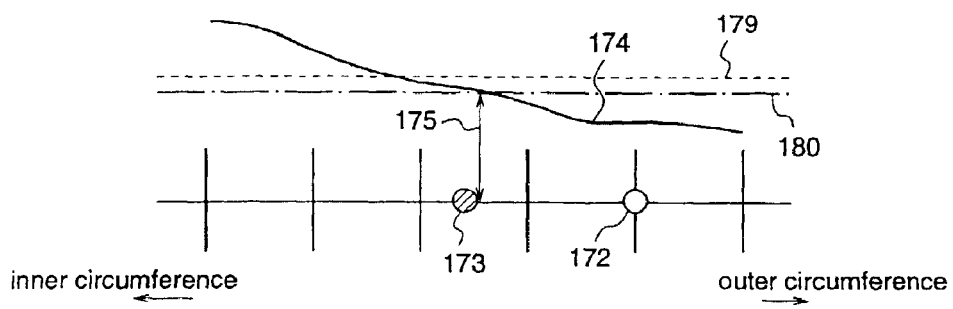
FIG. 17 is a diagram exemplifying a judgement of an offset threshold value of the optical disk drive according to the third embodiment of the present invention.

In FIG. 17, if the processing shifts to a read and a read error occurs in spite of a lens offset amount 175 at a seek end 173 that is smaller than a threshold offset value 179, the CPU 21 stores the lens offset amount 175 at this point of time to use it as a threshold offset value 180 for judging a seek end in the next read. Also after this, the threshold offset value for judging a seek end is updated every time a read error occurs, whereby a lens offset 174 can be converged to a maximum offset amount at which no error occurs at an actual read start position 172 while learning an offset amount at which a read error occurs and, therefore, unnecessary kickback is dispensed with to realize a stable read and improved access time.

As described above, the amount of offset from the center of the lens in the pickup at a point of time where a read error occurs is measured and stored, and not read, but kickback is performed until the offset amount at seek end becomes smaller than this stored offset value, whereby the maximum offset amount at which no error occurs can be obtained while learning an offset amount at which a read error occurs in the actual operation. Therefore, unnecessary kickback is dispensed with, and stable read and improved access time are realized.

Next, in order to make the third embodiment correspond to the invention according to the ninth aspect, a lower limit is provided to updation of the threshold offset value for judging a seek end. That is, the CPU 21, which constructs the seek position setting means, has a limiter for setting a lower limit value so that a value to be compared with the offset amount at seek end is not smaller than a predetermined value.

Figure 18:
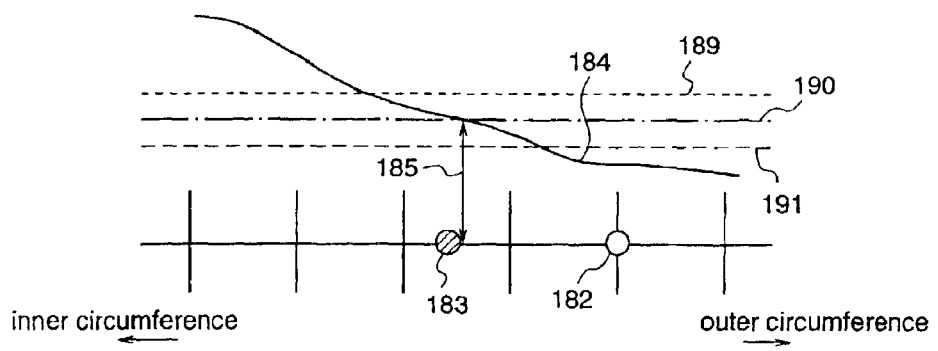
FIG. 18 is a diagram exemplifying a judgement of an offset threshold value of the optical disk drive according to the third embodiment of the present invention.

In FIG. 18, when the processing shifts to a read and a read error occurs in spite of a lens offset amount 185 at a seek end 183 that is smaller than a threshold offset value 189, the CPU 21 stores the lens offset amount 185 at this point of time to use it as a threshold offset value 190 for judging a seek end at the next read, while the offset amount is not updated and a lower limit value 191 of the offset amount is used as a threshold when the threshold offset value 190 is lower than the lower limit value 191 of the offset amount. Therefore, an offset amount 184 is not so large at an actual read start position 182, and the read is performed actively when it can be performed, whereby unnecessary kickback is dispensed with, resulting in an improvement in access time. As described above, the amount of offset from the center of the lens in the pickup at a point of time where a read error occurs is measured and stored, and not read, but kickback is performed until the offset amount at seek end becomes smaller than this stored offset value, while a lower limit is provided so that the stored offset amount is not smaller than a predetermined value. Therefore, the read is performed actively when it can be performed, whereby unnecessary kickback is dispensed with to improve access time.

While the first to third embodiments have been described taking a CD-ROM drive as an example, the present invention can be applied to all kinds of optical disk drives, and further, the present invention can be also applied to a seek followed by a write or the like in a recordable or rewritable optical disk drive as well as a seek followed by a read, and the same effects as those described for the first to third embodiments can be achieved.

APPLICABILITY IN INDUSTRY

As described above, a controller for driving a pickup of an optical disk drive according to the invention is useful for controlling driving of a pickup in a drive which performs read or write from/to an optical disk medium, such as a CD-ROM drive, and particularly, it is suited for controlling driving of a pickup so as to speedily cancel an offset of a lens which occurs due to a feed seek operation.

What is claimed is:

1. A controller for driving a pickup of an optical disk drive, the controller comprising:
   a lens offset measuring means for measuring an amount of offset of a lens from a center of the lens in the pickup, the lens offset occurring at a seek of the pickup; and
   a seek position setting means for setting a seek position where a seek toward a target position of the pickup is ended, based on the amount of lens offset measured by the lens offset measuring means and a number of seek tracks to seek.

2. A controller as defined in claim 1, wherein:
   the lens offset measuring means also measures a direction of the lens offset; and
   the seek position setting means sets the seek position also based on the direction of the lens offset and a direction of the seek.

3. A controller as defined in claim 1, wherein:
   the seek position setting means sets the seek position for a target position at least one sector before the target position.

4. A controller for driving a pickup of an optical disk drive, the controller comprising:
   a lens offset measuring means for measuring an amount of offset of a lens from a center of the lens in the pickup, the lens offset occurring at a seek of the pickup; and
   a seek position setting means for setting a seek position where a seek toward a target position of the pickup is ended based on the amount of lens offset measured by the lens offset measuring means and a number of seek tracks to seek, wherein the seek position setting means changes the seek position for a target position according to a rotation speed of a disk.

5. A controller for driving a pickup of an optical disk drive, the pickup being movably supported by a feed, the controller comprising:

a lens offset measuring means for measuring an amount and a direction of an offset of a lens from a center of the lens in the pickup at a seek end, and storing the amount and the direction of lens offset; and a seek position setting means for comparing an offset amount and an offset direction just before a seek with the offset amount and the offset direction stored in the lens offset measuring means when a number of seek tracks of a next seek is smaller than a predetermined value, thereby calculating a movement of the feed just before the seek as a calculation result and, based on the calculation result, setting a seek position where the seek toward a target position of the pickup is to be ended.

6. A controller as defined in claim 5, wherein:

the seek position setting means changes the seek position for the target position according to a rotation speed of a disk.

7. A controller as defined in claim 5, wherein:

the seek position setting means sets the seek position for the target position at least one sector before the target position.

8. A controller for driving a pickup of an optical disk drive, the controller comprising:

a lens offset measuring means for measuring an amount of offset of a lens from a center of the lens in the pickup; and a seek position setting means for setting a seek position where a seek toward a target position of the pickup is to be ended and a seek position at kickback so that kickback of the pickup for seeking in a direction inverse to a direction of the original seek is performed until an amount of lens offset at seek end becomes smaller than a predetermined value.

9. A controller for driving a pickup of an optical disk drive, the controller comprising:

a lens offset measuring means for measuring an amount of offset of a lens from a center of the lens in the pickup; and a seek position setting means for setting a seek position where a seek toward a target position of the pickup is to be ended and a seek position at kickback so that kickback of the pickup for seeking in a direction inverse to a direction of the original seek is performed until an amount of lens offset at seek end becomes smaller than a predetermined value, wherein the seek position setting means employs the amount of offset of the lens from the center of the lens in the pickup at a point in time where a read error occurs, as the predetermined value to be compared with the amount of lens offset at seek end.

10. A controller as defined in claim 9, wherein:

the seek position setting means has a limiter for setting a lower limit so that the predetermined value to be compared with the amount of lens offset at seek end does not become smaller than a predetermined minimum value.

* * * * *